(12) United States Patent
Shen et al.

(10) Patent No.: US 10,065,910 B2
(45) Date of Patent: Sep. 4, 2018

(54) METHOD FOR THE REDUCTION OF A SUGAR, SUGAR ALCOHOL OR GLYCEROL

(71) Applicant: Clariant Corporation, Louisville, KY (US)

(72) Inventors: Wenqin Shen, Louisville, KY (US); Franz Petzold, Louisville, KY (US); Karen Libby, Louisville, KY (US); Wayne Turbeville, Crestwood, KY (US); Matthew Purcell, Louisville, KY (US); Marc K. Born, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 15/463,911

(22) Filed: Mar. 20, 2017

(65) Prior Publication Data
US 2017/0190643 A1 Jul. 6, 2017

Related U.S. Application Data

(62) Division of application No. 14/267,948, filed on May 2, 2014.

(51) Int. Cl.
| | | |
|---|---|---|
| *C07C 29/132* | (2006.01) | |
| *B01J 23/755* | (2006.01) | |
| *B01J 23/72* | (2006.01) | |
| *B01J 23/75* | (2006.01) | |
| *B01J 23/745* | (2006.01) | |
| *B01J 23/06* | (2006.01) | |
| *B01J 23/83* | (2006.01) | |
| *B01J 23/44* | (2006.01) | |
| *B01J 23/843* | (2006.01) | |
| *B01J 35/00* | (2006.01) | |
| *B01J 37/03* | (2006.01) | |
| *B01J 37/04* | (2006.01) | |
| *B01J 37/02* | (2006.01) | |
| *B01J 37/00* | (2006.01) | |
| *B01J 37/08* | (2006.01) | |
| *B01J 37/06* | (2006.01) | |

(52) U.S. Cl.
CPC ............ *C07C 29/132* (2013.01); *B01J 23/06* (2013.01); *B01J 23/44* (2013.01); *B01J 23/72* (2013.01); *B01J 23/745* (2013.01); *B01J 23/75* (2013.01); *B01J 23/755* (2013.01); *B01J 23/83* (2013.01); *B01J 23/8435* (2013.01); *B01J 35/0006* (2013.01); *B01J 37/0009* (2013.01); *B01J 37/0215* (2013.01); *B01J 37/0236* (2013.01); *B01J 37/031* (2013.01); *B01J 37/04* (2013.01); *B01J 37/06* (2013.01); *B01J 37/08* (2013.01); *B01J 37/088* (2013.01)

(58) Field of Classification Search
CPC ..... C07C 29/132; B01J 23/8435; B01J 37/08; B01J 37/0009; B01J 37/0236; B01J 37/06; B01J 37/04; B01J 37/031; B01J 35/0006; B01J 37/088; B01J 23/44; B01J 23/83; B01J 23/06; B01J 23/745; B01J 23/75; B01J 23/72; B01J 23/755; B01J 37/0215
See application file for complete search history.

(56) References Cited

U.S. PATENT DOCUMENTS

| | | |
|---|---|---|
| 2,279,198 A | 4/1942 | Huppke |
| 5,002,922 A | 3/1991 | Irgang |
| 5,447,898 A | 9/1995 | Blankenstein |
| 5,672,558 A | 9/1997 | White |
| 7,297,321 B2 | 11/2007 | Shpeizer |
| 7,642,210 B2 | 1/2010 | Okamoto |
| 7,824,656 B2 | 11/2010 | Idem |
| 8,778,833 B2 | 7/2014 | Madon et al. |
| 9,132,418 B2 | 9/2015 | Shen |
| 2004/0179994 A1 | 9/2004 | Fenouil |
| 2006/0216227 A1 | 9/2006 | Idem |
| 2007/0036710 A1 | 2/2007 | Fenouil et al. |
| 2009/0305882 A1 | 12/2009 | Saint-Gobain Norpro |
| 2011/0009614 A1* | 1/2011 | Blommel ............ B01J 38/10 536/124 |
| 2011/0301021 A1 | 12/2011 | Liu et al. |
| 2011/0319672 A1 | 12/2011 | Liu et al. |
| 2012/0283459 A1 | 11/2012 | Kim et al. |

FOREIGN PATENT DOCUMENTS

| | | |
|---|---|---|
| CN | 101462057 | 6/2009 |
| WO | 9408914 | 4/1994 |
| WO | 2013162029 | 10/2013 |

OTHER PUBLICATIONS

Perez-Luna et al., "Study of alumina-promoted SO42—/NiO/ZrO2 catalyst performance," Catalysis Letters vol. 102, Nos. 1-2, Jul. 2005, pp. 33-38.
Hengne, Amol M., Green Chem., 14, 1064-1072 (2012), "Cu—ZrO2 nanocomposite catalyst for selective hydrogenation of levulinic acid and its ester to y-valerolactone."

* cited by examiner

*Primary Examiner* — Anthony J Zimmer

(57) ABSTRACT

The present disclosure relates generally to ceramic materials suitable for use as catalyst support materials, catalysts using such materials and methods for using them, such as methods for converting sugars, sugar alcohols, glycerol, and biorenewable organic acids to commercially-valuable chemicals and intermediates. One aspect of the invention is a ceramic material including zirconium oxide and one or more metal oxides selected from nickel oxide, copper oxide, cobalt oxide, iron oxide and zinc oxide, the ceramic material being at least about 50 wt. % zirconium oxide. In certain embodiments, the ceramic material is substantially free of any binder, extrusion aid or additional stabilizing agent.

24 Claims, 8 Drawing Sheets

METHOD FOR THE REDUCTION OF A SUGAR, SUGAR ALCOHOL OR GLYCEROL

CROSS-REFERENCE TO RELATED APPLICATIONS

Figure 1:
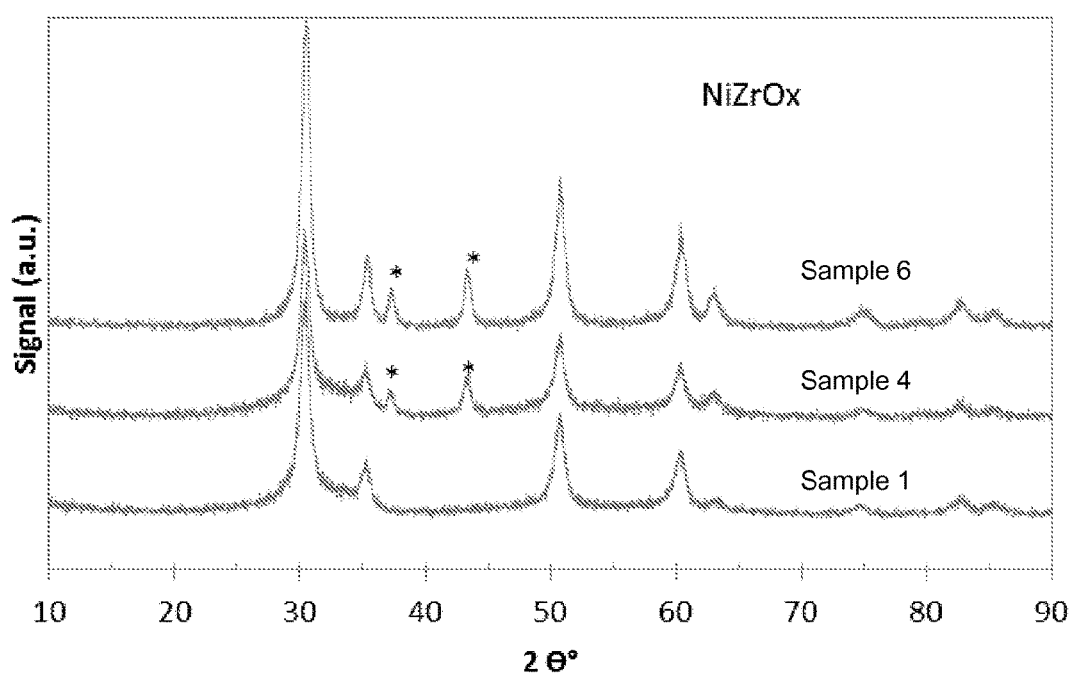

This application is a divisional of U.S. patent application Ser. No. 14/267,948, filed May 2, 2014, which is hereby incorporated herein by reference in its entirety.

BACKGROUND OF THE INVENTION

Field of the Invention

The present disclosure relates generally to ceramic materials, catalysts and methods for using them, such as methods for converting sugars, sugar alcohols, and glycerol to commercially-valuable chemicals and intermediates.

Technical Background

Zirconium oxide has been used as a support material in the field of chemical catalysis because of its high physical and chemical stability and moderately acidic surface properties. Nonetheless, the use of zirconium oxide as a supporting material for heterogeneous catalysts has limited application due to its relatively high cost and difficulties in forming certain shapes from. Furthermore, the zirconium oxide is especially susceptible to undergoing a phase transition that results in loss of surface area and pore volume. This reduces the strength and durability of the zirconium oxide. To counteract these phase transformation effects, stabilizing agents are used to inhibit phase transformation from the preferable tetragonal phase to the less desirable monoclinic phase. Previously used stabilizing agents include, for example, silicon oxide, yttrium oxide, lanthanum oxide, tungsten oxide, magnesium oxide, calcium oxide, cerium oxide, chromium oxide and manganese oxide.

Physical and chemical stability is a major concern in the application of heterogeneous catalysts in aqueous phase reactions. Traditional $SiO_2$ or $Al_2O_3$ based catalyst supports are prone to disintegration or attack when used in an aqueous solution, which usually results in loss of mechanical strength of the catalyst body that is targeted for a long-term industrial application. In laboratory and industrial applications, the mechanical strength of heterogeneous catalysts is generally evaluated by crush strength, wherein increasing crush strength values are generally indicative of improved mechanical strength of the support or carrier. Use of zirconium oxide promoted with chromium oxide promoter materials yields a zirconium oxide-based support or catalyst with improved physical properties for extrusion and/or use as a carrier or support for a catalyst in industrial applications performed in an aqueous environment. Chromium oxide-promoted zirconium oxide support or catalyst materials typically demonstrate no leaching into an aqueous solution, improving the mechanical strength and stability of the support/carrier or catalyst in various aqueous phase applications.

However, use of chromium-containing materials, especially chromium(VI) containing materials, is less desirable because of their toxic, corrosive, and carcinogenic properties. Manganese-containing materials are a viable alternative to chromium-containing materials, but their use as catalyst materials can often be limited to aqueous phase reactions with a product pH above 6. There remains a need environmentally nonhazardous materials that are also stable for aqueous phase applications at a wide range of pH values.

SUMMARY OF THE INVENTION

In certain aspects, the present invention addresses the need for a chromium-free catalyst or catalyst support suitable for aqueous phase applications. In various aspects, the disclosure provides a zirconium oxide-metal oxide material that is hydrothermally stable, suitable for use in aqueous phase reduction reactions, stable to low pH, and can be easily extruded in the absence of any binder and/or extrusion aid. The metal oxides in the material can in certain aspects serve as a textural promoter to stabilize zirconium oxide in aqueous phase, and serve as a promoter to improve the catalytic performance, and even themselves serve as a catalytic active component. In certain aspects, the materials are especially useful in aqueous phase hydrogenation and hydrogenolysis processes.

In one aspect, the disclosure provides a ceramic material comprising zirconium oxide and metal oxide, wherein the zirconium oxide is present within the range of about 50 wt. % to about 99 wt. % of the material; the metal oxide is one or more of nickel oxide, copper oxide, cobalt oxide, iron oxide and zinc oxide; and the metal oxide is present within the range of about 1 wt. % to about 50 wt. % of the material. The catalyst material can also be substantially free of any binder, extrusion aid or additional stabilizing agent.

In another aspect, the disclosure provides catalysts that include a ceramic material as described herein (e.g., as a catalyst support material), in combination with a catalytically active material. In certain embodiments, the catalytically active material can be a catalytic metal, e.g., Ni, Cu, Co, Fe, Ru, Rh, Pd, Ag, Re, Os, Ir, Pt, Au, Sb, La or any combination thereof, such as NiCu or NiSb.

In another aspect, the disclosure provides methods that utilize the ceramic materials and catalysts as described herein. As will be described below, in certain embodiments the ceramic materials and described herein are stable enough to be used in continuous aqueous phase reaction schemes, such as those in continuous stirrer tank reactors or fixed bed reactors. Accordingly, in one embodiment, a method for performing a catalytic reaction includes contacting one or more reactants with a ceramic material or catalyst as described herein, wherein at least one of the reactants is in the aqueous phase. In certain embodiments, the reaction is conducted at a temperature within the range of 50° C. to 325° C., and a pressure within the range of about 10 bar to about 250 bar.

In particular, the disclosure provides methods for reduction reactions, such as the hydrogenation or hydrogenolysis of sugars, sugar alcohols and glycerol. These reduction reactions include contacting the sugar, sugar alcohol or glycerol with hydrogen and a ceramic material or catalyst as described herein. For example, certain such methods include a process for converting a sugar, sugar alcohol or glycerol into a polyol or an alcohol comprising a shorter carbon-chain backbone by contacting the sugar, sugar alcohol or glycerol with hydrogen and a ceramic material or catalyst as described herein.

The disclosure also provides methods to use the ceramic materials or catalysts for the hydrogenation of an organic acid, e.g., in an aqueous phase. For example, certain such methods include a process for reducing an organic acid (e.g., lactic acid, succinic acid, adipic acid, 3-hydroxypropionic acid, and/or a sugar acid) by contacting the organic acid with hydrogen and a ceramic material or catalyst as described herein.

In another aspect, the disclosure also provides methods for preparing the ceramic materials and catalysts as described herein. For example, in one embodiment, a ceramic material is made by extruding a zirconium oxide-metal oxide precursor in the absence of any binder, extrusion aid or additional stabilizing agent. In one embodiment, a ceramic material is made by extruding a catalytically active material-zirconium oxide-metal oxide precursor in the absence of any binder, extrusion aid, or additional stabilizing agent. In another embodiment, a catalyst is made by depositing one or more catalytically active materials on to a zirconium oxide-metal oxide support material. Depositing may include, but is not limited to, impregnation, incipient wetness methods, precipitation, and physical mixing.

Specific embodiments of the present invention will become evident from the following detailed description of certain embodiments, examples, and the claims.

BRIEF DESCRIPTION OF THE SEVERAL VIEWS OF DRAWINGS

FIG. 1 provides the XRD patterns of nickel oxide-stabilized zirconium oxide ceramic materials containing 6.6 wt. %, 15 wt. % and 18 wt. % nickel (wt. % calculated as metallic Ni). XRD was performed after calcination at 450° C. for 3 h. The XRD patterns demonstrate that the crystalline content of the zirconium oxide is predominantly in a tetragonal phase. Peaks corresponding to NiO are marked with asterisks.

Figure 2:
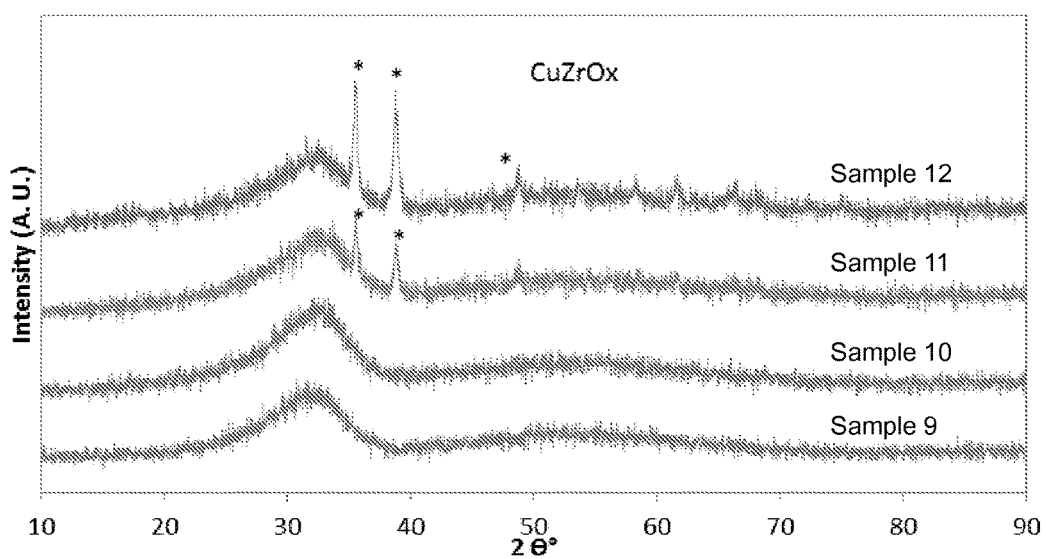

FIG. 2 provides the XRD patterns of copper oxide-stabilized zirconium oxide materials containing 16 wt. %, 23 wt. %, 28 wt. % and 32 wt. % copper (wt. % calculated as metallic Cu). XRD was performed after calcination at 450° C. for 3 h. The XRD patterns demonstrate that the crystalline content of the zirconium oxide is predominantly in an amorphous phase. Peaks corresponding to CuO are marked with asterisks.

Figure 3:
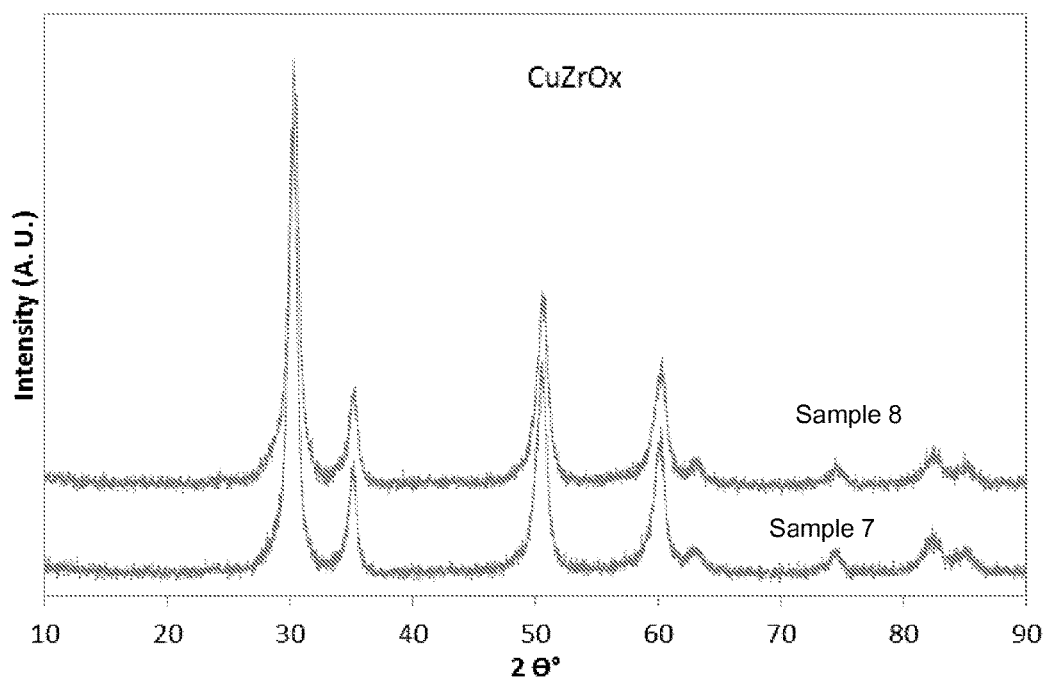

FIG. 3 provides the XRD patterns of copper oxide-stabilized zirconium oxide materials containing 6.5 wt. % and 7.5 wt. % copper (wt. % calculated as metallic Cu). XRD was performed after calcination at 550° C. for 3 h. The XRD patterns demonstrate that the crystalline content of the zirconium oxide is predominantly in a stabilized tetragonal phase. No CuO is observed.

Figure 4:
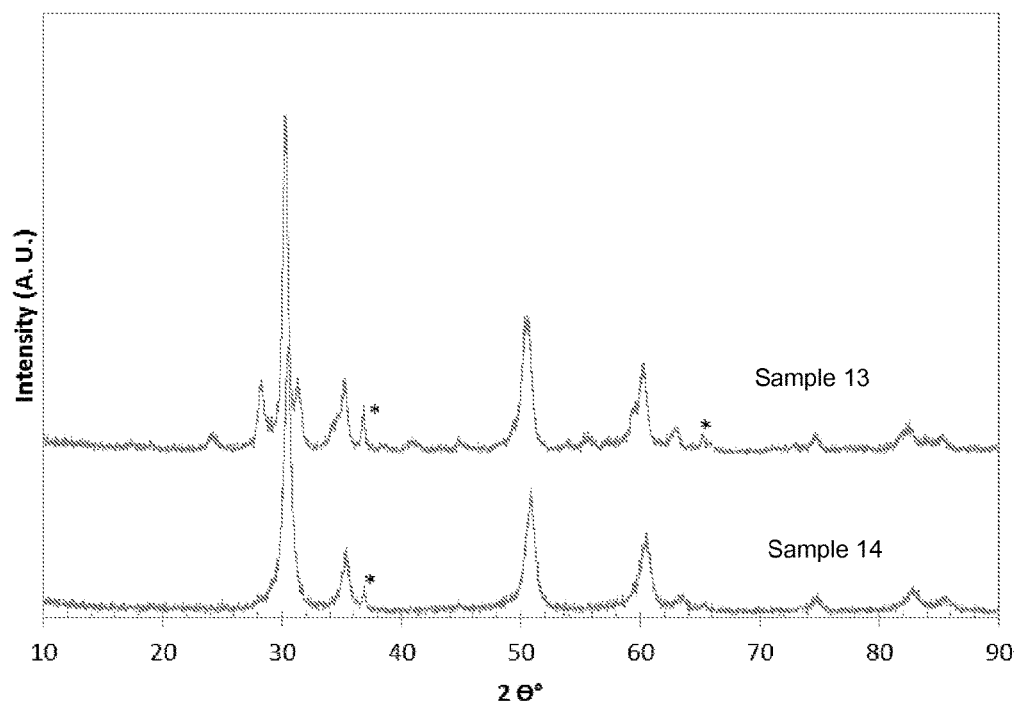

FIG. 4 provides XRD patterns of cobalt oxide-stabilized zirconium oxide materials containing 9.9 wt. % cobalt (wt. % calculated as metallic Co). XRD was performed after calcination at 450 and 600° C. for 3 h. The XRD patterns demonstrate that the crystalline content of the zirconium oxide is predominantly in a fully stabilized tetragonal phase. Peaks corresponding to $Co_3O_4$ are marked with asterisks.

Figure 5:
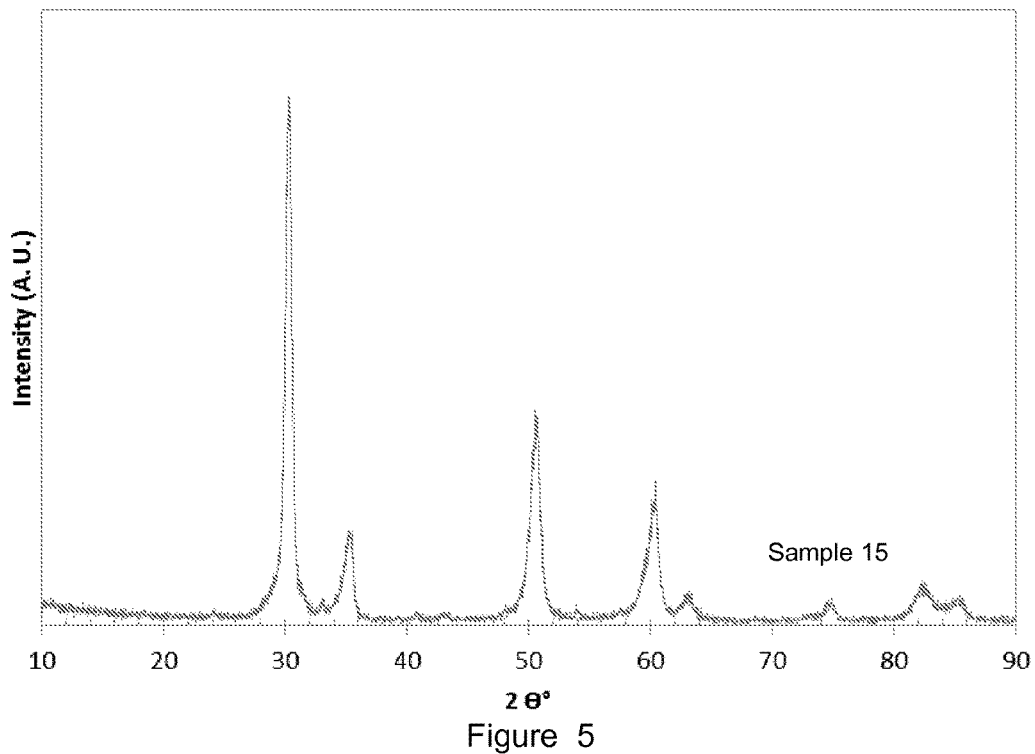

FIG. 5 provides the XRD pattern of an iron oxide-stabilized zirconium oxide material containing 9.9 wt. % iron (wt. % calculated as metallic Fe). XRD was performed after calcination at 600° C. for 3 h. The XRD patterns demonstrate that the crystalline content of the zirconium oxide is predominantly in a fully stabilized tetragonal phase.

Figure 6:
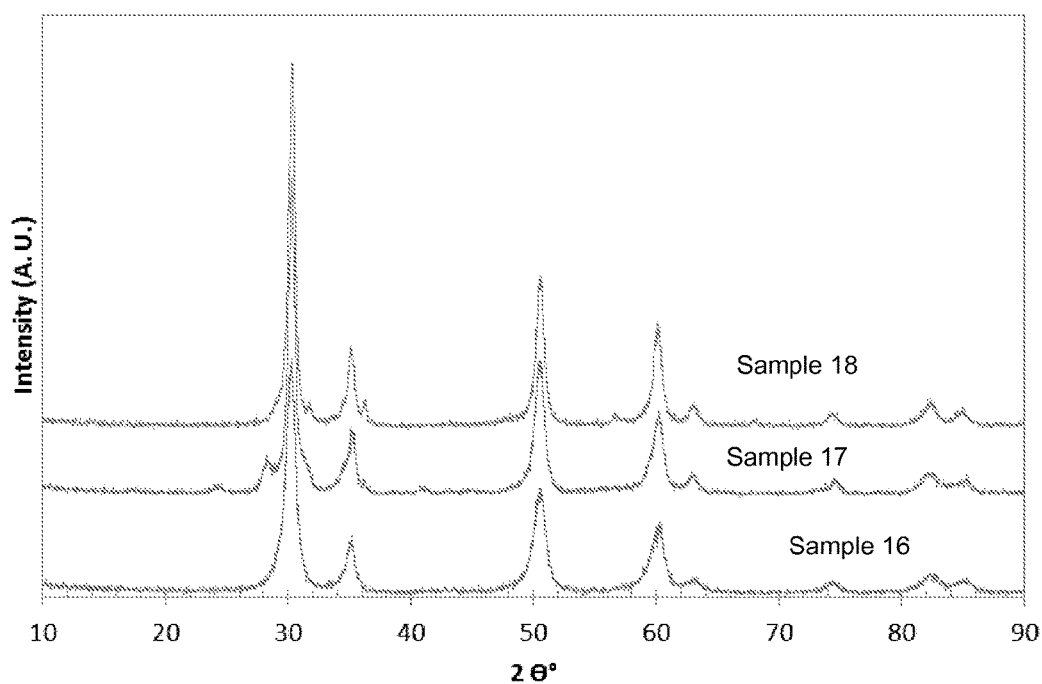

FIG. 6 provides the XRD patterns of zinc oxide-stabilized zirconium oxide materials containing 6 wt. % and 11 wt. % zinc (wt. % calculated as metallic Zn). XRD was performed after calcination at 450° C. and 550° C. for 3 h. All materials show a fully stabilized tetragonal phase as the crystalline content of the zirconium oxide. Zinc oxide was not observed.

Figure 7:
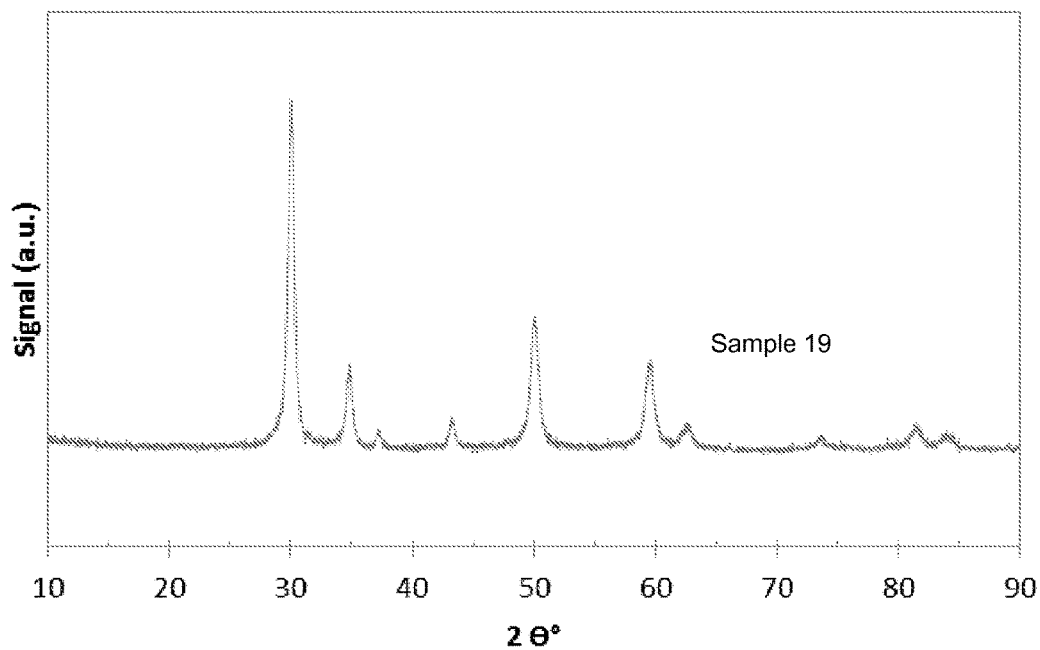

FIG. 7 provides the XRD pattern of a ternary phase zirconium oxide material containing 10 wt. % nickel and 10 wt. % lanthanum (wt. % calculated as metallic Ni and La, respectively). XRD was performed after calcination at 600° C. for 3 h. The XRD patterns demonstrate that the crystalline content of the zirconium oxide is predominantly in a fully stabilized tetragonal phase.

Figure 8:
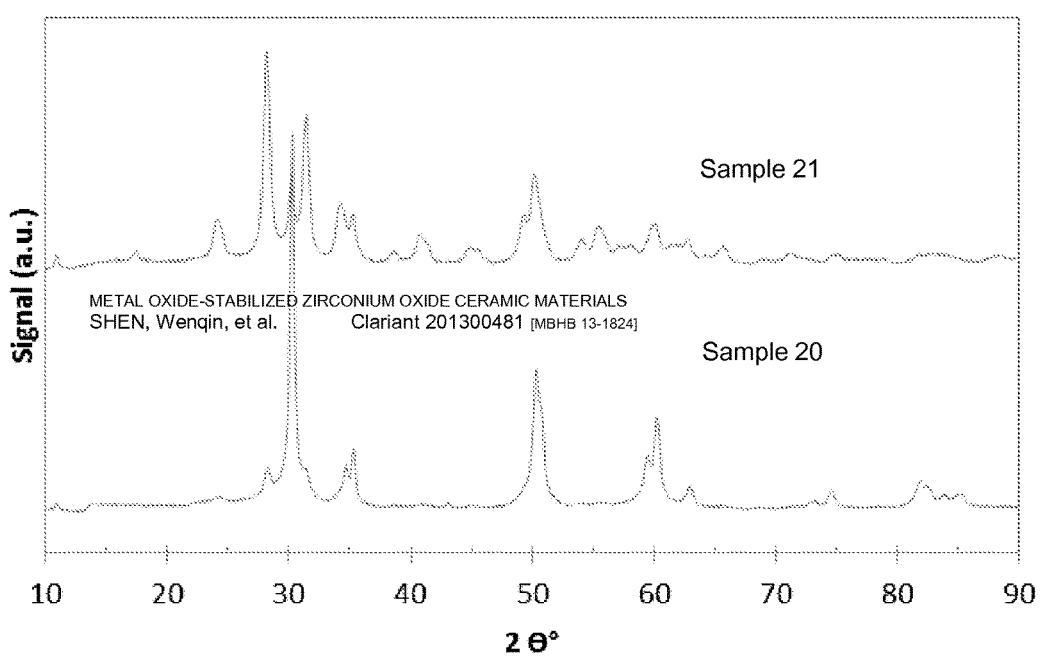

FIG. 8 provides the XRD patterns of a conventional zirconium oxide material. XRD was performed after calcination at 450° C. and 550° C. for 3 h. The XRD patterns demonstrate that the zirconium oxide is predominantly in a tetragonal phase when calcined at 450° C. and a monoclinic mixture when calcined at 550° C.

DETAILED DESCRIPTION OF THE INVENTION

Before the disclosed methods and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the active material). All mol % values are based on the moles of metal atoms.

In view of the present disclosure, the methods and materials described herein can be configured by the person of ordinary skill in the art to meet the desired need. In general, the disclosed materials, methods, and apparati provide improvements in supports or carriers utilized in catalysis, particularly in aqueous phase hydrogenolysis and hydrogenation. For example, in certain aspect, the materials are less environmentally hazardous than Cr-based materials, hydrothermally stable, suitable for use in continuous aqueous phase hydrogenolysis and hydrogenation, and can be easily extruded in the absence of any binder and/or extrusion aid.

One embodiment of the invention is a ceramic material including zirconium oxide (e.g., $ZrO_2$) and one or more metal oxides. The zirconium oxide is present in the ceramic material in an amount within the range of about 50 wt. % to about 99 wt. %. The metal oxide in the ceramic material is present in an amount within the range of about 1 wt. % to about 50 wt. %. The metal oxide is one or more of nickel oxide (wt. % calculated as metallic Ni); copper oxide (wt. % calculated as metallic Cu); cobalt oxide (wt. % calculated as metallic Co); iron oxide (wt. % calculated as metallic Fe); and zinc oxide (wt. % calculated as metallic Zn). As the person of ordinary skill in the art will appreciate, the zirconium oxide and the metal oxide are desirably substantially present together in the same phase of the material (e.g., as a mixed oxide $MZrO_x$). For example, in certain embodiments, at least 50%, at least 70% or even at least 90% of the metal oxide is present together in the same phase of the material as the zirconium oxide.

As will be described in more detail below, the ceramic materials described herein can be useful in the field of catalysis. For example, the ceramic materials described herein can be used as catalyst support materials, on which catalyst metals or metal compounds can be disposed. In other embodiments, the ceramic materials described herein can be used themselves as catalysts, either in their oxide form, or upon activation by reduction of part of the metal oxide to the corresponding metal.

In certain embodiments, the metal oxide is present in an amount (i.e., calculated on the metallic basis) within the range from about 1 wt. % to about 20 wt. %, or about 1 wt. % to about 15 wt. %, or about 1 wt. % to about 10 wt. %, or about 1 wt. % to about 8 wt. %, or about 1 wt. % to about 7 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %, or from about 3 to about 50 wt. %, or from about 10 to about 50 wt. %, or from about 15 to about 50 wt. %, or from about 3 to about 20 wt. %, or from about 10 to about 20 wt. %, or from about 15 to about 25 wt. %.

In certain embodiments, the zirconium oxide is present in an amount on the zirconium oxide basis within the range from about 80 wt. % to about 99 wt. %; from about 85 wt. % to about 99 wt. %; from about 90 wt. % to about 99 wt. %; from about 92 wt. % to about 99 wt. %; from about 93 wt. % to about 99 wt. %; from about 85 wt. % to about 97 wt. %; from about 90 wt. % to about 97 wt. %; from about 93 wt. % to about 97 wt. %; from about 93 wt. % to about 95 wt. %; from about 92 wt. % to about 95 wt. %; from about 90 wt. % to about 95 wt. %; from about 50 wt. % to about 97 wt. %; from about 50 wt. % to about 90 wt. %; from about 50 wt. % to about 85 wt. %; from about 80 wt. % to about 97 wt. %; from about 80 wt. % to about 90 wt. %; or from about 75 wt. % to about 85 wt. %.

As described above, the metal oxide can include oxides of iron, cobalt, nickel, copper or zinc. As the person of ordinary skill in the art will appreciate, the oxidation state of metal can be variable, and the metal can be present in one or more of a variety of oxidation states within the material. In some embodiments, the metal oxide is iron oxide. The iron oxide can be present as iron(II), iron (III) or a mixture thereof. For example, in one embodiment, the iron oxide is present as iron (II) oxide. In another embodiment, the iron oxide is present as iron (III) oxide. In other embodiments, the iron oxide is present as a mixed iron (II, III) oxide.

In certain embodiments (for example, when the metal oxide is iron oxide), the iron oxide is present in an amount on the Fe metallic basis within the range from about 1 wt. % to about 30 wt. %, about 1 wt. % to about 20 wt. %, or about 1 wt. % to about 15 wt. %, or about 1 wt. % to about 12 wt. %, or about 1 wt. % to about 10 wt. %, or about 1 wt. % to about 8 wt. %, or about 1 wt. % to about 7 wt. %, or about 1 wt. % to about 3 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %. In certain embodiments, the iron oxide is present in an amount within the range from about 5 wt. % to about 30 wt. % of the ceramic material.

In some embodiments, the metal oxide is cobalt oxide. The cobalt oxide can be present as cobalt(II), cobalt (III) or a mixture thereof. For example, in one embodiment, the cobalt oxide is present as cobalt (II) oxide. In another embodiment, the cobalt oxide is present as cobalt (III) oxide. In other embodiments, the cobalt oxide is present as a mixed cobalt (II, III) oxide.

In certain embodiments (for example, when the metal oxide is cobalt oxide), the cobalt oxide is present in an amount on the Co metallic basis within the range from about 1 wt. % to about 25 wt. %, or about 1 wt. % to about 15 wt. %, or about 1 wt. % to about 12 wt. %, or about 1 wt. % to about 10 wt. %, or about 1 wt. % to about 8 wt. %, or about 1 wt. % to about 7 wt. %, or about 1 wt. % to about 3 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %. In certain embodiments, the cobalt oxide is present in an amount within the range from about 5 wt. % to about 25 wt. % of the catalytic material.

In some embodiments, the metal oxide is nickel oxide. For example, in one embodiment, the nickel oxide is present as nickel (II) oxide.

In some embodiments (for example, when the metal oxide is nickel oxide), the nickel oxide is present in an amount on the Ni metallic basis within the range from about 1 wt. % to about 40 wt. %, or about 1 wt. % to about 30 wt. %, or about 1 wt. % to about 20 wt. %, or about 1 wt. % to about 15 wt. %, or about 1 wt. % to about 12 wt. %, or about 1 wt. % to about 10 wt. %, or about 1 wt. % to about 8 wt. %, or about 1 wt. % to about 7 wt. %, or about 1 wt. % to about 3 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %, or about 5 wt. % to about 20 wt. %, or about 5 wt. % to about 30 wt. %. In certain embodiments, the nickel oxide is present in an amount within the range from about 5 wt. % to about 20 wt. % of the catalytic material.

In some embodiments, the metal oxide is copper oxide. The copper oxide can be present as copper(I), copper(II) or a mixture thereof. For example, in one embodiment, the copper oxide is present as copper (I) oxide. In another embodiment, the copper oxide is present as copper (II) oxide. In other embodiments, the copper oxide is present as a mixed copper (I, II) oxide.

In some embodiments (for example, when the metal oxide is copper oxide), the copper oxide is present in an amount on the Cu metallic basis within the range from about 1 wt. % to about 40 wt. %, or about 1 wt. % to about 35 wt. %, or about 1 wt. % to about 30 wt. %, or about 1 wt. % to about 25 wt. %, or about 1 wt. % to about 20 wt. %, or about 1 wt. % to about 15 wt. %, or about 1 wt. % to about 10 wt. %, or about 1 wt. % to about 8 wt. %, or about 1 wt. % to about 7 wt. %, or about 1 wt. % to about 3 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %, or 15 wt. % to about 35 wt. %, or about 20 wt. % to about 35 wt. %, or about 25 wt. % to about 35 wt. %, or about 10 wt. % to about 35 wt. %, or about 10 wt. % to about 25 wt. %. In certain embodiments, the copper oxide is present in an amount within the range from about 5 wt. % to about 35 wt. % of the catalytic material.

In some embodiments, the metal oxide is zinc oxide. For example, in one embodiment, the zinc oxide is present as zinc (II) oxide.

In some embodiments (for example, when the metal oxide is zinc oxide), the zinc oxide is present in an amount on the Zn metallic basis within the range from about 1 wt. % to about 25 wt. %, or about 1 wt. % to about 20 wt. %, or about 1 wt. % to about 15 wt. %, or about 1 wt. % to about 12 wt. %, or about 1 wt. % to about 10 wt. %, or about 1 wt. % to about 8 wt. %, or about 1 wt. % to about 7 wt. %, or about 1 wt. % to about 3 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %. In certain embodiments, the zinc oxide is present in an amount within the range from about 5 wt. % to about 25 wt. % of the catalytic material.

Without intending to be bound by theory, the inventors believe that the metal oxide acts to stabilize the zirconium oxide from undergoing the undesirable phase transition from the preferable tetragonal phase to the less desirable monoclinic phase. Accordingly, the ratio of zirconium oxide to the metal oxide can be important for the performance of the ceramic material.

In certain embodiments of the catalyst materials and methods as described herein, at least about 70 wt. % of the ceramic material is the zirconium oxide and the one or more metal oxides. For example, in certain embodiments of the materials and methods as described herein, at least about 80 wt. %, at least about 90 wt. %, at least about 95 wt. %, at least about 99 wt. %, at least about 99.5 wt. % or even at least about 99.9 wt. % of the ceramic material is the zirconium oxide and the one or more metal oxides.

The ceramic materials described herein can be made without chromium but still provide zirconium oxide stabilized in a tetragonal phase, thus providing more environmentally benign materials. Accordingly, in some embodiments of the materials and methods as described herein, the material is substantially free of chromium.

In some embodiments of the materials and methods as described herein, the materials are substantially free of manganese and oxides thereof.

In certain embodiments of the ceramic materials described herein, other metal oxides (i.e., other than oxides of nickel, copper, cobalt, iron and zinc) can be included. Additional non-reducible metal oxides can include, for example, oxides of yttrium, lanthanum, cerium, niobium, tungsten, molybdenum, titanium, calcium, magnesium, boron, tin, anitmony and mixtures thereof. As the person of ordinary skill in the art will appreciate, such other metal oxides may be used to provide additional desirable properties to the ceramic material, for example tuning the acidity/basicity of the catalytic materials, or improving the metal oxides used herein dispersion, or improving the reducibility, improving the texture properties. The other reducible metal oxides can also be used as precursors for a catalytic metal, described in more detail below. Reducible metal oxides suitable for use as catalytic metal precursors include, e.g., palladium, platnium, iridinium, rhenium, silver and ruthenium. In embodiments in which the ceramic material includes one more additional metal oxides, the additional metal oxide can be present in an amount on metal basis up to about 15 wt. %, for example, up to about 12 wt. %, up to about 10 wt. %, up to about 8 wt. %, up to about 7 wt. %, up to about 3 wt. %, up to about 1 wt. % or up to about 0.05 wt. %. In some embodiments, the additional metal is present in an amount within the range from about 0.05 wt. % to about 12 wt. %, or about 0.05 wt. % to about 10 wt. %, or about 0.05 wt. % to about 8 wt. %, or about 0.05 wt. % to about 7 wt. %, or about 3 wt. % to about 15 wt. %, or about 3 wt. % to about 10 wt. %, or about 3 wt. % to about 7 wt. %, or about 5 wt. % to about 7 wt. %, or about 5 wt. % to about 8 wt. %, or about 5 wt. % to about 10 wt. %, or about 10 wt. % to about 15 wt. %.

In certain embodiments of the catalyst materials and methods as described herein, at least about 70 wt. % of the ceramic material is the zirconium oxide and the one or more metal oxides (i.e., including the one or more additional metal oxides). For example, in certain embodiments of the materials and methods as described herein, at least about 80 wt. %, at least about 90 wt. %, at least about 95 wt. %, at least about 99 wt. %, at least about 99.5 wt. % or even at least about 99.9 wt. % of the ceramic material is the zirconium oxide and the one or more metal oxides (i.e., including the one or more additional metal oxides).

In certain embodiments, a ceramic material as described herein includes (or, in one embodiment, consists essentially of) zirconium oxide in an amount (calculated on the basis of $ZrO_2$) within the range of about 50 to about 99 wt. %; one or more of nickel oxide, copper oxide, cobalt oxide, iron oxide and zinc oxide, in an amount on the metallic basis within the range of about 1 wt. % to about 50 wt. %; and optionally one or more additional metal oxides in an amount up to about 15 wt. %. For example, in a particular embodiment, a ceramic material as described herein includes (or, in one embodiment, consists essentially of) zirconium oxide in an amount within the range of about 70 to about 99 wt. %; one or more of nickel oxide, copper oxide, cobalt oxide, iron oxide and zinc oxide, in an amount on the metallic basis within the range of about 1 wt. % to about 30 wt. %; and optionally one or more additional metal oxides in an amount on the metallic basis up to about 15 wt. %. In another particular embodiment, a ceramic material as described herein includes (or, in one embodiment, consists essentially of) zirconium oxide in an amount on the basis of zirconium oxide within the range of about 75 to about 99 wt. %; one or more of nickel oxide, copper oxide, cobalt oxide, iron oxide and zinc oxide, in an amount on the metallic basis within the range of about 1 wt. % to about 25 wt. %; and optionally one or more additional metal oxides in an amount on the metallic basis up to about 15 wt. %. For example, in a particular embodiment, a ceramic material as described herein includes (or, in one embodiment, consists essentially of) zirconium oxide in an amount on the basis of zirconium oxide within the range of about 80 to about 99 wt. %; one or more of nickel oxide, copper oxide, cobalt oxide, iron oxide and zinc oxide, in an amount on the metallic basis within the range of about 1 wt. % to about 20 wt. %; and optionally one or more additional metal oxides in an amount on the metal basis up to about 15 wt. %. In another particular embodiment, a ceramic material as described herein includes (or, in one embodiment, consists essentially of) zirconium oxide in an amount on the basis of zirconium oxide within the range of about 85 to about 99 wt. %; one or more of nickel oxide, copper oxide, cobalt oxide, iron oxide and zinc oxide, in an amount on the metallic within the range of about 1 wt. % to about 12 wt. %; and optionally one or more additional metal oxides in an amount on metallic basis up to about 10 wt. %. In certain such embodiments, the ceramic material includes (or, in one embodiment, consists essentially of) zirconium oxide in an amount on the basis of zirconium oxide within the range of about 90 wt. % to about 99 wt. %; a metal oxide in an amount on metallic basis within the range of about 1 wt. % to about 8 wt. %;

optionally one or more additional metal oxides in an amount on metallic basis up to about 5 wt. %.

As will be described in more detail below, the ceramic material may be made via a number of different techniques familiar to the person of ordinary skill in the art. The ceramic material can be made with a variety of crystalline forms, such as one or more of monoclinic, tetragonal, cubic and/or amorphous phases as determined by well-known powder x-ray diffraction (XRD) techniques and devices (e.g., see "Introduction to X-ray Powder Diffraction," R. Jenkins and R. L Snyder, Chemical Analysis, Vol. 138, John Wiley & Sons, New York, 1996). However, in certain advantageous embodiments, the zirconium oxide in the ceramic material as described herein is predominantly (e.g., greater than about 50%, greater than about 70%, greater than about 80%, greater than about 90%, or even greater than about 95%) in a phase having either tetragonal geometry or amorphous phase, or a combination thereof, and has a relatively minor amount (e.g., less than about 50%, less than about 30%, less than about 20%, less than about 10%, or even less than about 5%) of zirconium oxide in the monoclinic phase, in order to maintain the desired mechanical strength and physical properties to be used as a catalytic material.

The ceramic materials as described herein may be provided in any suitable form. For example, in various embodiments, a ceramic material as described herein can be formed as spheres, pellets, cylinders (hollow or otherwise), symmetrical or asymmetrical tri-quadrulobes, for example, using extrusion methods as described below. The person of ordinary skill in the art will appreciate that the ceramic materials can be provided in a variety of other forms.

The ceramic materials described herein can be provided with a variety of different pore volumes, depending, e.g., on the methods used for making them and the desired end use. For example, in certain embodiments, a ceramic material as described herein has a pore volume within the range of about 0.1 to about 0.6 cm$^3$/g, or about 0.2 to about 0.5 cm$^3$/g, or about 0.3 to about 0.5 cm$^3$/g, or about 0.4 to about 0.6 cm$^3$/g, or about 0.1 to about 1 cm$^3$/g. In various embodiments, a ceramic material as described herein has a pore volume of about 0.1 cm$^3$/g, or about 0.2 cm$^3$/g, or about 0.3 cm$^3$/g, or about 0.4 cm$^3$/g, or about 0.5 cm$^3$/g, or about 0.6 cm$^3$/g. In particular embodiments, the ceramic material has a pore volume within the range of about 0.2 to about 0.5 cm$^3$/g. In other particular embodiments, the ceramic material has a pore volume within the range of about 0.2 to about 0.4 cm$^3$/g.

Similarly, the ceramic materials described herein can be provided with a variety of different surface areas, depending, e.g., on the methods used for making them and the desired end use. For example, in certain embodiments, the surface area of a ceramic material as described herein within the range of about 10 to about 400 m$^2$/g. The surface areas are measured using the Brunauer-Emmett-Teller (BET) Surface Area method. In certain embodiments, a ceramic material as described herein has a surface area within the range of from about 10 to about 400 m$^2$/g, or about 50 to about 400 m$^2$/g, or about 70 to about 400 m$^2$/g, or about 100 to about 400 m$^2$/g, or about 200 to about 400 m$^2$/g, or about 300 to about 400 m$^2$/g, or about 10 to about 300 m$^2$/g, or about 50 to about 300 m$^2$/g, or about 70 to about 300 m$^2$/g, or about 100 to about 300 m$^2$/g, or about 200 to about 300 m$^2$/g, or about 10 to about 200 m$^2$/g, or about 50 to about 200 m$^2$/g, or about 70 to about 200 m$^2$/g, or about 100 to about 200 m$^2$/g. In one embodiment, a ceramic material as described herein has a surface area of about 25 to about 250 m$^2$/g. In another embodiment, a ceramic material as described herein has a surface area of about 50 to about 150 m$^2$/g. In another embodiment, a ceramic material as described herein has a surface area of about 30 to about 120 m$^2$/g.

The ceramic materials described herein can be provided with a variety of different crush strengths, depending, e.g., on the methods used for making them and the desired end use. For example, in certain embodiments, a ceramic material as described herein has a crush strength within the range of about 45 N/cm (i.e., ~1 lb/mm) to about 450 N/cm (i.e., ~10.0 lb/mm.) For example, in certain embodiments, a ceramic material as described herein has a crush strength of at least 45 N/cm (i.e., ~1 lb/mm), or at least 67 N/cm (i.e., ~1.5 lb/mm), or at least 90 N/cm (i.e., ~2 lb/mm), or at least 134 N/cm (i.e., ~3 lb/mm), or at least 178 N/cm (i.e., ~4 lb/mm), depending on its use. In various embodiments, a ceramic material as described herein has a crush strength within the range of about 45 N/cm to about 178 N/cm, or about 45 N/cm to about 134 N/cm, or about 45 N/cm to about 90 N/cm, or about 45 N/cm to about 67 N/cm, or about 67 N/cm to about 178 N/cm, or about 67 N/cm to about 134 N/cm, or about 67 N/cm to about 90 N/cm, about 90 N/cm to about 178 N/cm, or about 90 N/cm to about 134 N/cm. The crush strength of a material is measured using ASTM D6175-03 (2008), Standard Test Method for Radial Crush Strength of Extruded Catalyst and Catalyst Carrier Particles.

As will be described in further detail below, certain ceramic materials as described herein can be prepared, for example, using extrusion methods without the use of any binder, extrusion aid or additional stabilizing agent. Accordingly, in certain embodiments, a ceramic material as described herein is substantially free of any binder. In other embodiments, a ceramic material as described herein is substantially free of any extrusion aid. For example, in one particular embodiment, a ceramic material as described herein is substantially free of any binder and any extrusion aid. Moreover, as the metal oxide can stabilize the zirconium oxide, in certain embodiments, a ceramic material as described herein can be substantially free of an additional stabilizing agent. In certain embodiments, a ceramic material as described herein is substantially free of any binder, extrusion aid or additional stabilizing agent. For example, in certain embodiments, a ceramic material as described herein is substantially free of silicon dioxide, aluminum compounds, silica-alumina compounds, graphite and carbon black. In all such embodiments, the ceramic material can be provided as an extrudate.

The ceramic materials described herein can be made using a variety of techniques. For example, in one embodiment a co-precipitation technique is used to make a ceramic material as described herein. A zirconium compound and one or more metal oxide precursor compounds can be combined in aqueous solution and co-precipitated with base to co-precipitate a zirconium oxide-metal oxide precursor. Alternatively, the zirconium compound may be precipitated first and then the metal oxide precursor compound may be mixed with the precipitated zirconium oxide precursor to form the zirconium oxide-metal oxide precursor. Metal oxide precursors can also be added (for example, at relatively low levels, e.g., when they are to be used as a catalyst metal precursor) via well-known impregnation techniques. The zirconium oxide-metal oxide precursor can then be dried, shaped and calcined in accordance with well-known processes to form a finished ceramic material.

A variety of zirconium-containing compounds can be used as starting materials. For example, the zirconium compound may be selected from the group consisting of zirconium or zirconyl halides, zirconium or zirconyl nitrates, zirconium or zirconyl organic acids, and combinations thereof. Specific compounds include, for example, $ZrCl_4$, $ZrOCl_2$, $Zr(NO_3)_2 \cdot 5H_2O$, $ZrO(NO_3)_2$ and $ZrO(CH_3COO)_2$. Of course, as the person of ordinary skill in the art will appreciate, other zirconium compounds can be used; the processes described herein are not limited to the compounds specifically identified herein. In solution, zirconium can be in a form of zirconyl ($ZrO^{2+}$) or zirconium ion ($Zr^{4+}$ or $Zr^{2+}$) that may be obtained by dissolving corresponding salts in water.

A wide variety of metal-containing compounds can be used as the metal oxide precursor. Metal compounds can be, for example, in the form of halides, nitrates or organic acid salts similar to those described above with respect to the zirconium compound. For example, the metal oxide precursor compound for iron can be $Fe(NO_3)_3$. Other metal oxide precursors are described below with respect to the Examples, and would be evident to the person of ordinary skill in the art. In other embodiments (e.g., when the metal oxide precursor compound is combined with the precipitated zirconium oxide precursor), the metal oxide precursor compound can be provided as the metal oxide itself.

Similarly, the optional additional metal oxides (e.g., of yttrium, lanthanum, cerium, niobium, tungsten, molybdenum, titanium, calcium, magnesium, boron, tin, anitmony silver, rhenium, ruthenium, palladium, rhodium, and iridium) can be incorporated into the zirconium oxide-metal oxide precursor by including corresponding salts in the solution to be precipitated, by impregnation, or by mixing of metal oxide precursor (e.g., the metal oxide itself) with the precipitated material. The salts can be, for example, in the form of halides, nitrates or organic acid salts similar to those described above with respect to the zirconium starting material and metal oxide precursor compound. For example, lanthanum can be introduced as lanthanum nitrate hexahydrate. Other metal oxide precursors are described below with respect to the Examples, and would be evident to the person of ordinary skill in the art.

In a co-precipitation method for making the ceramic materials as described herein, the zirconium compound and the metal oxide precursor compound are dissolved, together with any other additional metal oxide precursors in aqueous solution. A base (e.g., ammonia, ammonium hydroxide, sodium carbonate or sodium hydroxide) is then added to precipitate the zirconium oxide-metal oxide precursor at a pH in the range of about 6 to about 10. In some examples, the base is 25 wt. % NaOH and the pH of final precipitation is between about 7 and about 10. the pH of final precipitation is between about 8 and about 9. The person of ordinary skill in the art will select appropriate conditions depending on the starting materials, the desired end product, and the particular procedures used.

After the precipitation, the zirconium oxide-metal oxide precursor precipitate may be filtered or otherwise separated from the liquid. A variety of methods and/or apparatuses may be utilized, including the use of filter paper and vacuum pump, as well as centrifugal separation, other vacuum mechanisms and/or positive pressure arrangements. Optionally, the zirconium oxide-metal oxide precursor may be washed if any of the feed materials used in the process contain undesirable elements or compounds, such as chloride or sodium. Typically, one to ten washings, or even more washings may be desirable if undesired elements or other contaminants are present in the feed materials.

The zirconium oxide-metal oxide precursor can then be dried, using a variety of techniques and conditions as would be apparent to the person of ordinary skill in the art. The drying of the zirconium oxide-metal oxide precursor (e.g., when provided as a solid mass such as a filter cake) may be aided by dividing (e.g., breaking) it into smaller quantities. The division (e.g. breaking) of the filter-cake may be manual or automated. The zirconium oxide-metal oxide precursor may be dried at ambient conditions (e.g., room temperature and ambient pressure) or under moderate temperatures ranging up to about 120° C. In one embodiment, the zirconium-metal oxide precursor is dried at a temperature ranging between 40° C. and 90° C. for about 20 minutes to 20 hours, depending on the drying equipment used. As will be appreciated by the person of ordinary skill in the art, the zirconium oxide-metal oxide precursor can be dried to a level that is desirable for a subsequent forming step. In some embodiments, it may be desirable to leave the zirconium oxide-metal oxide precursor a little wet to aid in forming.

After being dried to a suitable level, the zirconium oxide-metal oxide precursor can be formed into any shape suitable for a catalyst support/carrier, using any of the forming methods familiar to the person of ordinary skill in the art. For example, in a particular embodiment of a method for making the ceramic materials as described herein, the dried zirconium oxide-metal oxide precursor is formed by being extruded through a suitable die. Extrusion methods are well-known in the art. For example, a screw extruder, a press extruder, or any other extrusion devices and/or methods known in the art may be used. Alternatively, the zirconium oxide-metal oxide precursor may be formed by pressing, tableting, pelleting, granulating, or even spray drying; the person of ordinary skill in the art will adjust the wetness of the zirconium oxide-metal oxide precursor to be suitable for the particular forming process used. Optionally, the extruded or otherwise formed zirconium oxide-metal oxide precursor may be further dried (for example, at moderate temperatures, e.g., up to about 120° C., for example, for a moderate period of time, e.g., typically about 1 to 5 hours) after being formed.

To convert the extruded or otherwise formed zirconium oxide-metal oxide precursor into a ceramic material, the zirconium oxide-metal oxide precursor can be calcined. For example, in certain embodiments of methods for making the ceramic materials as described herein, the extruded or otherwise formed zirconium oxide-metal oxide precursor is ceramic at a temperatures within the range of about 300° C. to about 1000° C., or in another embodiment, of about 400° C. to about 700° C. In various embodiments of methods for making the ceramic materials as described herein, the extruded or otherwise formed zirconium oxide-metal oxide precursor is calcined at a temperature within the range of about 300° C. to about 1000° C., or of about 400° C. to about 700° C., or of about 500° C. to about 600° C., or of about 400° C. to about 500° C., or of about 400° C. to about 600° C., or of about 500° C. to about 700° C., or of about 600° C. to about 700° C. The calcination may last, for example, for a time within the range of about 2 to about 12 hours, or about 3 to about 5 hours, e.g., about 3 hours, about 4 hours, about 5 hours, or about 6 hours. In certain embodiments of methods for making the ceramic materials as described herein, an extruded or otherwise formed zirconium oxide-metal oxide precursor is ceramic at about 600° C. As is conventional in the art, a variety of heating programs can be used in calcining. For example, in certain embodiments, a slow temperature ramp may be used to avoid thermal shock of the material. In one particular embodiment, an extruded or otherwise formed zirconium oxide-metal oxide precursor as described herein may be calcined with heating at a rate of 1° C. per minute to 600° C. at which temperature the calcining continues for about 3 hours. Based on the Examples described herein, the person of ordinary skill in the art can identify appropriate calcination conditions to provide the desired ceramic material.

Certain particular methods for making ceramic materials are described below in the Examples; the person of ordinary skill in the art can adapt these methods for making the ceramic materials described generally herein.

The ceramic materials as described herein may be provided in combination with one or more catalytically active materials to form a catalyst. Accordingly, another aspect of the invention is the ceramic material described herein used as a catalyst support material, with a catalytically active material disposed thereon. The catalytically active material can be, for example, a catalytic metal. In certain embodiments, a catalyst includes the ceramic material as described herein, and one or more catalytic metals selected from the group consisting of Ni, Cu, Co, Fe, Ru, Rh, Pd, Ag, Re, Os, Ir, Pt, Au, Sb, La or any combination thereof. In certain embodiments, the catalytic metal is one or more of nickel, copper and antimony. For example, the catalytic metal can be NiCu or NiSb. Of course, the person of ordinary skill in the art will appreciate that the catalyst support materials can be useful with other catalysts, for example, palladium, platinum, rhodium and ruthenium. Catalytic metals can be provided via impregnation, plating or deposition, or via reduction (e.g., in situ) of part of the metal oxide of the ceramic material.

The ceramic materials and catalysts described herein can, in certain embodiments, exhibit high hydrothermal and mechanical stability, and thus can be suitably durable for advantageous use in reduction reactions, such as aqueous phase hydrogenation or hydrogenolysis reactions, which include the reduction of sugars, sugar alcohols or glycerol. Accordingly, additional aspects of the invention relate to various uses of the ceramic materials and catalysts described herein. For example, one embodiment of the invention is a method of conducting a catalytic reaction including contacting one or more reactants with a catalyst as described herein, wherein at least one of the reactants is in the aqueous phase. Such reactions can, in certain embodiments, be conducted at relatively high temperatures (e.g., in the range of 50° C. to 325° C., or in the range of about 90° C. to about 275° C.), and/or at relatively high pressures (e.g., in the range of about 10 bar to about 250 bar, or in the range of about 50 bar to about 200 bar). In certain embodiments, at least one reactant is a gas (e.g., hydrogen), provided at partial pressure that is at least about 20%, at least about 50%, or even at least about 90% of the overall pressure.

As described above, the ceramic materials and catalysts described herein can, in certain embodiments, be stable at a wide variety of pH values. Accordingly, the methods described herein can be performed at a variety of pH values, including acidic pH values. For example, in one embodiment, a reaction as described herein is conducted such that the pH of the reaction mixture is (at some point during the process) in the range of about 2 to about 10, for example, in the range of about 2 to about 6, or about 2.5 to about 5. The process can be performed such that the ceramic material or catalyst is in contact with the reaction mixture at such pH values for at least about 1 minute, at least about 2 minutes, at least about 10 minutes, or even at least about 30 minutes.

The ceramic materials and catalysts described herein can be especially useful in catalytic hydrogenation or hydrogenolysis of a sugar, a sugar alcohol, or glycerol, for example, into commercially-valuable chemical products and intermediates, including, but not limited to, polyols or an alcohol comprising a shorter carbon-chain backbone such as propylene glycol (1,2-propanediol), ethylene glycol (1,2-ethanediol), glycerin, trimethylene glycol (1,3-propanediol), methanol, ethanol, propanol and butanediols. As used herein, unless otherwise qualified, the term polyol(s) refers to any polyhydric alcohol containing more than one hydroxyl group. As broadly defined, the term polyol may encompass both the reactants and/or the products described above.

In one embodiment of a catalytic method as described herein, a sugar, a sugar alcohol or glycerol is contacted with a source of hydrogen and a ceramic material or catalyst as described herein. As the person of ordinary skill in the art will appreciate, the source of hydrogen can be hydrogen gas.

The ceramic materials and catalysts described herein can also be useful in catalytic hydrogenation of organic acids into commercially-valuable chemical products and intermediates. Exemplary organic acids include, but are not limited to, acetic acid, formic acid, propionic acid, butyric acid, caproic acid, glycolic acid, lactic acid, 3-hydroxypropionic acid, hydroxylbutyric acid, hydroxycyclopentanoic acid, salicylic acid, mandelic acid, benzoic acid, fatty acids, and sugar acids. As used herein, unless otherwise noted, the term sugar acid(s) refers to any monosaccharide containing one or more carboxylic acid moieties. Examples include, but are not limited to glyceric acid, xylonic acid, gluconic acid, ascorbic acid, tartaric acid, mucic acid, saccharic acid, glucuronic acid, and galacturonic acid. The organic acids may also include polycarboxylic acid compounds, such as tartaric acid, citric acid, malic acid, oxalic acid, succinic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphthalic acid, dihydroxyfumaric acid, tricarballylic acid, benzene-1,3,5-tricarboxylic acid, isocitric acid, mucic acid and glucaric acid. In one embodiment of the disclosure, the organic acid is selected from lactic acid, succinic acid, adipic acid, and various sugar acids. Thus, one embodiment of a catalytic method as described herein includes contacting an organic acid and hydrogen gas with a catalyst as described herein (e.g., with Ni, Cu, Co, Fe, Ru, Rh, Pd, Ag, Re, Os, Ir, Pt, Au, Sb, La or any combination thereof as the catalytic metal). The contacting can be performed at a relatively high temperature and/or pressure as described above. The catalysts described herein can be made by any suitable method. For example, a catalytically active material (e.g., a catalytic metal) can be disposed on a catalyst support material as described herein using conventional methods, for example, by depositing the catalytically active material thereon. Depositing may include, but is not limited to, impregnation, incipient wetness, precipitation, and physical mixing. Alternatively, the catalytically active material can be provided at any stage in the formation of the catalyst (e.g., as the catalytically active material or as some precursor for the catalytically active material that gets converted to catalytically active material in a later step).

EXAMPLES

The following examples are presented to illustrate the embodiments of the present invention and are not intended to constitute a limitation on their scope, which is defined in the appended claims.

Example 1: Nickel-Stabilized Zirconium Oxide Materials

Nickel-stabilized zirconium oxide materials were prepared by co-precipitation of a nickel nitrate ($Ni(NO_3)_2$) and zirconyl nitrate (ZrO(NO$_3$)$_2$) precursor solution using a sodium hydroxide solution. For a typical preparation, Sample 6 of Table 1 below as an example, 550 g nickel nitrate solution (13.8 wt. % nickel on metal basis) was premixed with 1665 g zirconyl nitrate solution (equivalent to 20 wt. % zirconium oxide) and precipitated with a 25 wt. % NaOH solution. The precipitation was conducted at a constant pH ranging from 6-10, typically, 8-9 at room temperature with vigorous stirring. The precipitate was aged overnight (about 16 h) and washed with excess de-ionized water until the conductivity of the final filtered water was less than 0.4 mS/cm. The precipitate was dried accordingly and the resulting material was extruded using an auger extruder. The extrudates were dried at 110° C. for 3 h, followed by calcination at a temperature ranging from 400-650° C. for 2-5 h.

Table 1 lists the physical properties of six preparations, Samples 1-6. Nickel content on metal basis varied from 6.6 wt. % to approximately 18 wt. % as analyzed by XRF bulk analysis. All extrudates exhibited good crush strength (above 1.9 lb/mm) and a pore volume of 0.15 to 0.22 mL/g. The Brunauer-Emmett-Teller surface area (BET S.A.) varied from about 50 m$^2$/g to about 120 m$^2$/g with the variation of calcination temperature, precipitation pH and aging time.

TABLE 1

Properties of nickel oxide-stabilized zirconium oxide extrudates.

| Sample No. | Ni wt. %[1] | Crush Strength (lb/mm) | Pore Volume (mL/g) | BET S.A. (m$^2$/g) | Attrition % | Calcination Temp. (° C.) |
|---|---|---|---|---|---|---|
| 1 | 6.6 | 2.8 | 0.2 | 49 | 2.6 | 450 |
| 2 | 10.0 | 5.4 | 0.15 | 119 | <1.0 | 450 |
| 3 | 10.0 | 8.6 | 0.17 | 50 | <1.0 | 600 |
| 4 | 15.0 | 1.9 | 0.18 | 114 | 6.6 | 450 |
| 5 | 15.0 | 1.9 | 0.18 | 80 | <1.0 | 600 |
| 6 | 18.0 | 2.1 | 0.22 | 45 | 2.9 | 450 |

[1]Weight percent of Ni calculated as metallic Ni.

FIG. 1 shows the XRD pattern of the selected nickel-stabilized zirconium oxide materials (Samples 1, 4 and 6). After calcination at 450° C. for 3 h, the nickel-stabilized zirconium oxide materials exhibit predominantly tetragonal phase zirconium oxide patterns as well as NiO peaks (marked with asterisks) in the higher nickel content materials.

Example 2: Copper-Stabilized Zirconium Oxide Materials

Copper-stabilized zirconium oxide materials were prepared by co-precipitation of a copper nitrate and zirconyl nitrate precursor solution using a sodium hydroxide solution. For a typical preparation, Sample 10 as an example, 467 g copper nitrate (Cu(NO$_3$)$_2$) solution (15.5 wt. % Cu on metal basis) was premixed with 1169 g zirconyl nitrate solution (equivalent to 20 wt. % ZrO$_2$) and precipitated with a 25 wt. % NaOH solution. The precipitation was conducted at a constant pH ranging from 6-10, typically, 8-9 at room temperature with vigorous stirring. The precipitate was aged overnight (about 16 h) and washed with excess de-ionized water until the conductivity of the final filtered water was less than 0.4 mS/cm. The cake was dried, and the resulting dried material was extruded using an auger extruder. The extrudates were dried at 110° C. for 3 h, followed by calcination at a temperature ranging from 400-600° C. for 2-5 h.

Table 2 lists six of the preparations and the related physical properties. Cu content on metal basis varied from 6.5 wt. % to approximately 32 wt. % as analyzed by XRF bulk analysis. All extrudates showed good crush strength above 2.3 lb/mm and a pore volume of 0.2 mL/g to 0.5 mL/g. The Brunauer-Emmett-Teller surface area (BET S.A.) varied from about 50 to approximately 200 m$^2$/g for the resulting materials due to the variation in calcination temperature and precipitation pH.

TABLE 2

Properties of copper-stabilized zirconium oxide extrudates.

| Sample No. | Cu wt. %[1] | Crush Strength (lb/mm) | Pore Volume (mL/g) | BET S.A. (m$^2$/g) | Attrition % | Calcination Temp. (° C.) |
|---|---|---|---|---|---|---|
| 7 | 6.5 | 2.8 | 0.37 | 85 | 2.1 | 550 |
| 8 | 7.5 | 2.3 | 0.46 | 85 | 2.3 | 550 |
| 9 | 16.0 | 5.5 | 0.37 | 149 | 1.5 | 450 |
| 10 | 23.0 | 2.5 | 0.48 | 218 | 5.4 | 450 |
| 11 | 28.0 | 6.8 | 0.25 | 52 | 2.0 | 450 |
| 12 | 32.0 | 5.2 | 0.32 | 113 | 2.0 | 450 |

[1]Weight percent of Cu calculated as metallic Cu.

FIG. 2 provides the XRD patterns of the copper-stabilized zirconium oxide materials calcined at 450° C. (Samples 9-12). Zirconium oxide is in the form of an amorphous phase. With higher copper loadings of 28% and 32%, CuO peaks (marked with asterisks) are also observed. FIG. 3 provides the XRD patterns of copper-stabilized zirconium oxide materials calcined at 550° C. (Samples 7 and 8). A fully stabilized tetragonal phase of zirconium oxide was evident in the copper-stabilized zirconium oxide having 6.5% and 7.5% Cu content (calculated as metallic Cu).

Example 3: Cobalt-Stabilized Zirconium Oxide Materials

Cobalt-stabilized zirconium oxide materials were prepared by precipitation of a cobalt nitrate hexahydrate and zirconyl nitrate mixed precursor solution using a sodium hydroxide solution. For a typical preparation (i.e., the preparation of Samples 13 and 14), 120 g Co(NO$_3$)$_2$.6H$_2$O was premixed with 1040 g zirconyl nitrate solution (20 wt. % ZrO$_2$) and precipitated with a 25 wt. % NaOH solution. The precipitation was conducted at a constant pH ranging from 6-10, typically, 8-9 at room temperature with vigorous stirring. The precipitate was aged overnight (about 16 h) and washed with excess de-ionized water until the conductivity of the final filtered water was less than 0.4 mS/cm. Then, the cake was dried appropriately. The resulting dried material was extruded using an auger extruder. The extrudates so-formed were dried at 110° C. for 3 h, followed by calcination at a temperature ranging from 400-600° C. for 2-5 h.

Table 3 lists two such preparations (Samples 13 and 14) and their physical properties. Cobalt content was about 10 wt. % on metal basis as analyzed by XRF bulk analysis. The extrudates exhibited good crush strength above 1.2 lb/mm and a pore volume of about 0.4 g/mL. The Brunauer-Emmett-Teller surface area (BET S.A.) varied from about 32 to approximately 90 m$^2$/g, depending significantly on calcination temperature, precipitation pH and aging time.

TABLE 3

Properties of the cobalt-stabilized zirconium oxide extrudates.

| Sample No. | Co wt. %[1] | Crush Strength (lb/mm) | Pore Volume (mL/g) | BET S.A. (m$^2$/g) | Attrition % | Calcination Temp. (° C.) |
|---|---|---|---|---|---|---|
| 13 | 9.9 | 1.9 | 0.40 | 32 | 2.0 | 600 |
| 14 | 9.9 | 1.2 | 0.46 | 90 | 2.0 | 450 |

[1]Weight percent of Co calculated as metallic Co.

FIG. 4 provides the XRD patterns of the cobalt-stabilized zirconium oxide materials calcined at 450° C. and 600° C. Zirconium oxide is in the form of fully or partially stabilized tetragonal phase. In addition to zirconium oxide peaks, cobalt oxide ($Co_3O_4$) was also detected. The amount of cobalt oxide particles grew with calcination temperature from 450° C. to 600° C. Due to the decreased concentration of cobalt oxide in the zirconium oxide lattice, part of the stabilized tetragonal zirconium oxide phase reverted to monoclinic zirconium oxide in the material calcined at 600° C. (Sample 13).

Example 4: Iron-Stabilized Zirconium Oxide Materials

Iron-stabilized zirconium oxide materials were prepared by precipitation of an iron nitrate nonahydrate and zirconyl nitrate mixed precursor solution using a 25 wt. % sodium hydroxide solution. For a typical preparation (i.e., the preparation of Sample 15), 147 g $Fe(NO_3)_3.9H_2O$ was premixed with 885 g zirconyl nitrate solution (20 wt. % $ZrO_2$) and precipitated with a 25 wt. % NaOH solution. The precipitation was conducted at a constant pH ranging from 6-10, typically, 8-9 at room temperature with vigorous stirring. The precipitate was aged overnight (about 16 h) and washed with excess de-ionized water until the conductivity of the final filtered water was less than 0.4 mS/cm. Then, the cake was dried appropriately. The resulting dried material was extruded using an auger extruder. The extrudates so-formed were dried at 110° C. for 3 h, followed by calcination at a temperature ranging from 400-600° C. for 2-5 h.

Table 4 lists one of the preparations for iron-stabilized zirconium oxide and its physical properties. Fe content was about 9.9 wt. % on metal basis as analyzed by XRF bulk analysis. The extrudates are relatively weak with a crush strength around 0.6 lb/mm. The Brunauer-Emmett-Teller surface area (BET S.A.) was 148 m$^2$/g and the pore volume is about 0.5 g/mL.

TABLE 4

Properties of the iron-stabilized zirconium oxide extrudate.

| Sample No. | Fe wt. %[1] | Crush Strength (lb/mm) | Pore Volume (mL/g) | BET S.A. (m$^2$/g) | Attrition % | Calcination Temp. (° C.) |
|---|---|---|---|---|---|---|
| 15 | 9.9 | 0.6 | 0.50 | 148 | 5.1 | 600 |

[1]Weight percent of Fe calculated as metallic Fe.

FIG. 5 shows the XRD patterns of the iron stabilized zirconium oxide materials calcined at 600° C. Zirconium oxide is in the form of a fully stabilized tetragonal phase.

Example 5: Zinc-Stabilized Zirconium Oxide Materials

Zinc-stabilized zirconium oxide materials were prepared by precipitation of a zinc nitrate hexahydrate and zirconyl nitrate mixed precursor solution using a sodium hydroxide solution. For a typical preparation, 60.5 g $Zn(NO_3)_2.6H_2O$ was premixed with 1052 g zirconyl nitrate solution (20 wt. % $ZrO_2$) and precipitated with a 25 wt. % NaOH solution. The precipitation was conducted at a constant pH ranging from 6-10, typically, 8-9 at room temperature with vigorous stirring. The precipitate was aged overnight (about 16 h) and washed with excess de-ionized water until the conductivity of the final filtered water was less than 0.4 mS/cm. Then, the cake was dried appropriately. The resulting drying material was extruded using an auger extruder. The extrudates so-formed were dried at 110° C. for 3 h, followed by calcination at temperature ranging from 400-600° C. for 2-5 h.

Table 5 lists three of the preparations for zinc-stabilized zirconium oxide and their physical properties. Zn content was varied from 6% to 11% on metal basis as analyzed by XRF bulk analysis. The extrudates are strong with crush strength above 2 lb/mm for samples calcined at 550° C. By lowering the calcination temperature to 450° C., the surface area was significantly increased from 40 to 110 m$^2$/g. The pore volume of the resulting materials was about 0.2-0.4 g/mL depending on composition, calcination profile, precipitation pH and aging time.

TABLE 5

Properties of zinc-stabilized zirconium oxide extrudates.

| Sample No. | Zn wt. %[1] | Crush Strength (lb/mm) | Pore Volume (mL/g) | BET S.A. (m$^2$/g) | Attrition % | Calcination Temp. (° C.) |
|---|---|---|---|---|---|---|
| 16 | 6.0 | 1.5 | 0.36 | 113 | 1.4 | 450 |
| 17 | 6.0 | 2.0 | 0.36 | 45 | 1.2 | 550 |
| 18 | 11.0 | 2.9 | 0.26 | 46 | 2.1 | 550 |

[1]Weight percent of Zn calculated as metallic Zn.

FIG. 6 provides the XRD patterns of the Zn-stabilized zirconium oxide materials of Table 5. The materials were calcined at 450° C. and 550° C. for 3 h, respectively. A stabilized tetragonal phase was seen over all the materials. No isolated zinc oxide was observed.

Example 6: Ternary Zirconium Oxide Ceramics

The above-described approaches can be easily applied to prepare ternary materials. For example, a nickel/lanthanum-stabilized zirconium oxide material was prepared by precipitation of nickel nitrate solution (13.8 wt. % nickel on metal basis), lanthanum nitrate hexahydrate and zirconyl nitrate mixed precursor solution using a sodium hydroxide solution. In this preparation, 85 g $La(NO_3)_3.6H_2O$ and 205 g nickel nitrate solution was premixed with 1031 g zirconyl nitrate solution (20 wt. % $ZrO_2$) and precipitated with a 25 wt. % NaOH solution. The precipitation was conducted at a constant pH range from 6-10, typically, 8-9 at room temperature with vigorous stirring. The precipitate was aged overnight (about 16 h) and washed with excess de-ionized water until the conductivity of the final filtered water was less than 0.4 mS/cm. Then, the cake was dried appropriately. The resulting dried material was extruded using an auger extruder. The extrudates so-formed were dried at 110° C. for 3 h, followed by calcination at a temperature ranging from 400-600° C. for 2-5 h.

Table 6 lists two of the preparations for ternary zirconium oxide materials and the related physical properties. The extrudates are strong with good crush strength above 2.0 lb/mm and a pronounced surface area.

TABLE 6

Properties of nickel/lanthanum-stabilized zirconium oxide extrudates.

| Sample No. | Composition wt. %[1] | Crush Strength (lb/mm) | Pore Volume (mL/g) | BET S.A. (m²/g) | Attrition % | Calcination Temp. (° C.) |
|---|---|---|---|---|---|---|
| 19 | Ni: 10; La: 10 | 2.4 | 0.22 | 62 | 3.3 | 600 |
| 20 | Ni: 18; La: 6 | 3.1 | 0.17 | 141 | 5.3 | 450 |

[1]Weight percent of composition calculated on metallic basis

FIG. 7 provides XRD patterns of a ternary zirconium oxide ceramic (Sample 19) in a stabilized tetragonal phase. This material was calcined at 600° C. for 3 h.

Example 7: Comparison Experiment with Zirconium Oxide

Pure zirconium oxide was prepared by using the same precipitation approach in order to compare to the metal oxide stabilized zirconium oxide. The properties of the $ZrO_2$ extrudates calcined at 450° C. and 550° C. are shown in Table 7. The materials showed a very weak crush strength and became powder after finger pressing. The attrition is more than 40%. As used herein, attrition is defined as loss of fines through abrasion, which is wearing, grinding, or rubbing of the particles with each other or with container walls. The test is performed as described in ASTM D4058, which is hereby incorporated herein by reference, or alternately by manually shaking 5-10 grams of material vigorously/evenly in a closed 30 mL plastic container for 5 min and measure the loss of fines by sieving through a 16 mesh sieve, e.g. as described in Pure & Appl. Chem., Vol. 63, No. 9, 1227-1246 (1991) which is hereby incorporated herein by reference. The pure $ZrO_2$ extrudate prepared by the method above in the absence of any binder and extrusion aid is not suitable for use as a shaped carrier.

TABLE 7

Properties of $ZrO_2$ extrudates.

| Sample No. | Crush Strength (lb/mm) | Pore Volume (mL/g) | BET S.A. (m²/g) | Attrition % | Calcination Temp. (° C.) |
|---|---|---|---|---|---|
| 21 | <0.3 | 0.14 | 34.1 | >40 | 450 |
| 22 | <0.3 | 0.18 | 39.3 | >40 | 550 |

FIG. 8 provides XRD patterns of zirconium oxide prepared in the same approach with varied calcination temperatures. The XRD patterns in FIG. 8 shows the phase transition from tetragonal zirconium oxide to a mixture of tetragonal and monoclinic mixture with the increased calcination temperature on a pure zirconium oxide material.

Example 8: Glycerin Hydrogenolysis

In this Example, copper-stabilized zirconium oxide Samples 9, 10, and 11 were used directly as a catalyst for glycerin hydrogenolysis in an aqueous phase solution.

The feed (100 mL) contained about 40 wt. % glycerin with initial pH of 6.8. Catalyst was first sized to 10-14 mesh size. About 6.5-7.0 g catalyst was loaded into the reactor basket and reduced in-situ at 220° C. for 2 h with a slow heating ramp rate of 0.5 K/min and a hydrogen GHSV of 2000 $h^{-1}$. The test was conducted at 220° C. under 100 bar hydrogen pressure for 6 h. The product was sampled every one to 2 h during the test. T4466, a commercial CuCr catalyst, was also studied for glycerin hydrogenolysis at the same testing condition. This catalyst was reduced at 185° C. for 2 h with a slow heating ramp rate of 0.5 K/min and a hydrogen GHSV of 2000 $h^{-1}$.

Cobalt-stabilized zirconium oxide Sample 14 was also studied for glycerin hydrogenolysis under the exactly same conditions. The cobalt-stabilized zirconium oxide sample was reduced at 480° C. for 2 h with a heating ramp rate of 5 K/min and a hydrogen GHSV of 1000 $h^{-1}$.

The testing results are summarized in Table 8. The characterization of the spent catalysts are summarized in Table 9. All copper-stabilized zirconium oxide materials demonstrated significant higher activity than cobalt-stabilized zirconium oxide and T4466, a commercial CuCr catalyst. Sample 10 had the highest activity with conversion above 80%. The selectivity to propylene glycol (PG) through glycerin hydrogenolysis was above 85% over the copper-stabilized zirconium oxide catalysts. T4466 demonstrated 99% selectivity to 1.2 PG. However, the conversion was only about 12%. The ICP analysis for the aqueous product after 6 h reaction demonstrated no leaching of Cu into the solution for the copper-stabilized zirconium oxide samples even though the product pH was as low as 2.8. In contrast, 20 ppm Co was detected and 2 ppm Cu was detected over a cobalt-stabilized zirconium oxide sample and T4466.

The decrease of pore volume and surface area were observed in the spent copper-stabilized zirconium oxide samples. All of the spent samples maintained good crush strength.

TABLE 8

Summary of the testing results for glycerin hydrogenolysis over the studied catalysts. The tests were conducted at 220° C. for 6 h under 100 bar hydrogen pressure in a batch reactor. The feed was 100 mL of 40 wt. % glycerin aqueous solution.

| Test No. | Sample No. | Glycerin Hydrogenolysis (6 h) Conversion % | 1, 2 PG selectivity % | product pH (6 h) | Leaching |
|---|---|---|---|---|---|
| 1 | 10 | 88.2 | 84.4 | 3.0 | Cu: non-detectable |
| 2 | 10 | 80.6 | 88.1 | 3.0 | Cu: non-detectable |
| 3 | 9 | 73.6 | 89.9 | 2.8 | Cu: non-detectable |
| 4 | 11 | 76.5 | 87.8 | 3.7 | Cu: non-detectable |
| 5 | 14 | 37.7 | 85.2 | 3.2 | Co: 20 ppm |
| 6 | T4466 | 11.9 | 99 | 4.5 | Cu: 2 ppm |

TABLE 9

Characterization of the spent copper-stabilized zirconium oxide for glycerin hydrogenolysis. T4466, a comercial CuCr catalyst, is also listed for comparison.

| Sample No. | Composition wt. % (XRF)[1] Cu | Other | BET S.A. m²/g | P.V. cm³/g | Crush Strength lbs/mm |
|---|---|---|---|---|---|
| 10 (spent) | 23 | — | 113 | 0.29 | 2.50 |
| 9 (spent) | 16 | — | 123 | 0.28 | 5.98 |
| 11 (spent) | 30 | — | 106 | 0.16 | 6.27 |

TABLE 9-continued

Characterization of the spent copper-stabilized zirconium oxide for glycerin hydrogenolysis. T4466, a comercial CuCr catalyst, is also listed for comparison.

| Sample No. | Composition wt. % (XRF)[1] | | BET S.A. $m^2/g$ | P.V. $cm^3/g$ | Crush Strength lbs/mm |
|---|---|---|---|---|---|
| | Cu | Other | | | |
| T4466 (unused) | 45 | Cr: 29 | 45.2 | 0.19 | 16.7 lbs* |
| T4466 (spent) | 45 | Cr: 29 | 83.9 | 0.13 | 10.2 lbs* |

[1]Weight percent of composition calculated on metallic basis.

Note:
T4466 are tablet and was size to 10-14 mesh in irregular shape.

Example 9: Sugar Hydrogenation

Sugar hydrogenation to sugar alcohol is an industrial important process. This process is carried out in the aqueous phase. Accordingly, catalyst stability in aqueous phase under elevated temperature and pressure is highly desirable, especially for a fixed bed continuous process.

Nickel-stabilized zirconium oxide (Sample 4) and nickel/lanthanum-stabilized zirconium oxide (Sample 19) were studied for xylose hydrogenation. A palladium promoted nickel-stabilized zirconium oxide (No. 4) was also studied for xylose hydrogenation in order to boost the catalytic activity. Pd promoted $NiZrO_x$-No. 4 was prepared by conventional incipient wetness method. The desired amount of palladium nitrate hydrate (Pd: 39 wt. %) was first dissolved in water and dropped into $NiZrO_x$-No. 4, followed by drying at 110° for 2 h and calcination at 450° C. for 2 h. The test was conducted in a fixed bed reactor with an O.D. of 1 inch. 30 mL of each catalyst was loaded into the reactor with a 1:1 volumetric dilution of SiC (40-60 mesh). All the catalysts were activated at 450° C. for 4 hours with a heating ramp rate of 3 K/min under a flow of pure hydrogen with GHSV of 1000 $h^{-1}$. The feed contained food grade xylose (Danisco USA Inc) and the pH was adjusted by diluted sodium carbonate before being pumped into the reactor. The detailed testing conditions are listed in table 10. The tests were conducted at 110° C. under 80 bar or 120 bar of hydrogen pressure with a flow of hydrogen (hydrogen/xylose=10 by mol. ratio) for more than 200 h. All the catalysts demonstrated steady state performance during the test. At a lower operation pressure of 80 bar, the catalyst was evaluated by using an 8 wt. % xylose solution. At 120 bar, the xylose concentration was increased to 20 wt. %. All the catalysts showed in excess of 99.9% conversion and in excess of 98% selectivity. For Test 9, the catalyst demonstrated about 100% selectivity to xylitol over the Pd (0.2 wt. %) promoted nickel-stabilized zirconium oxide (No. 4) catalyst. The catalysts are chemically very stable under this hydrothermal condition with no evident leachingtion.

TABLE 10

The testing conditions and the average catalytic performance for xylose hydrogenation over the nickel-stabilized zirconium oxide, nickel/lanthium-stablized zirconium oxide and palladium promoted nickel-stabilized zirconium oxide catalysts. The metal content in the aqueous product is also shown as a reference for chemical stability of the catalysts.

| Test | 7 | 8 | 9 |
|---|---|---|---|
| Catalyst | Sample 4 | Sample 4 | Pd/No. 4 |
| Operating Conditions | 80 Bar $H_2$ | 80 Bar $H_2$ | 120 Bar $H_2$ |
| | LHSV: 1 $h^{-1}$ | LHSV: 1 $h^{-1}$ | LHSV: 0.8 $h^{-1}$ |
| | 110° C. | 110° C. | 110° C. |
| | 8 wt. % Xylose | 8 wt. % Xylose | 20 wt. % Xylose |
| pH of Product | 5.75 | 6.35 | 4.50 |
| HOS | 211 h | 211 h | 279 h |
| Xylose Conversion % | 99.96 | 99.99 | 99.99 |
| CS to Xylitol % | 98.19 | 99.01 | 100.0 |
| Stability | No deactivation | No deactviation | No deactivation |
| Leaching study | Ni < 2 ppm; | Ni < 1 ppm, | Ni < 1 ppm, |
| | Zr < 1 ppm | La < 1 ppm; | Pd < 1 ppm; |
| | | Zr < 1 ppm | Zr < 1 ppm |

TABLE 11

Characterization of the spent catalysts for xylose hydrogenation.

| Sample No. | Composition wt. %[1] | BET S.A. $m^2/g$ | P.V. $cm^3/g$ | Crush Strength lbs/mm | XRD Phase |
|---|---|---|---|---|---|
| 4 (spent) | Ni: 15.8% | 79.2 | 0.16 | 1.43 | Ni; tetragonal $ZrO_2$ |
| 19 (spent) | Ni: 10.8%; La: 9.8% | 64.7 | 0.22 | 1.99 | Ni; tetragonal $ZrO_2$ |
| Pd/No. 4 (spent) | Ni: 13.2%, Pd: 0.2% | 76.56 | 0.15 | 1.90 | Ni; tetragonal $ZrO^2$ |

[1]Weight percent of composition calculated on metallic basis.

The spent catalysts were unloaded easily from the reactor and maintained good physical integrity. All of the spent catalysts demonstrated XRD peaks characteristic of FCC nickel metal and fully-stabilized tetragonal zirconium oxide. The crush strength, surface area, and the pore volume of the spent catalysts decreased slightly with no major inverse impact.

Example 10: Sugar Alcohol Hydrogenolysis

A NiSb catalyst was developed on a nickel-stabilized zirconium oxide material (Sample 1), which originally contained about 6.6 wt. % nickel on metal basis. The catalyst was made by a conventional impregnation method. The nickel-stabilized zirconium oxide (Sample 1, 50 g) was immersed in a mixed solution of nickel nitrate, antimony acetate and citric acid for 1 h and the leftover solution was decanted. The resulting material was then dried at 110° C. for 2 h and calcined at 450° C. for 2 h. To make the mixed precursor solution, antimony acetate was first dissolved in citric acid aqueous solution (citric acid/Sb=4, by mol. ratio) with stirring. The solution was then mixed with a nickel nitrate solution (13.8 wt. % on metal basis).

The xylitol hydrogenolysis test was conducted in a fixed bed reactor with an O.D. of 0.5 inch. 15 mL of the catalyst was loaded into reactor with a 1:1 volumetric dilution with SiC (60-80 mesh). The catalysts were activated at 450° C. for 4 hours with a heating ramp rate of 3 K/min under a flow of pure hydrogen with GHSV of 1000 $h^{-1}$. The feed contained food grade xylitol (Danisco USA Inc) and the pH was adjusted propriety by a diluted NaOH solution before being pumped into the reactor. The detailed testing conditions are listed in Table 11. The tests were conducted at 210° C. under 120 bar of hydrogen pressure with a flow of hydrogen (hydrogen/xylitol=10 by mol. ratio) for 210 h. The liquid hour space velocity was maintained at 3 $h^{-1}$. Xylitol/NaOH ratio (mol.) in feed was controlled at about 10, which yielded a mixed solution at a pH of 12.4. The catalysts demonstrated steady state performance during the test. The average conversion was about 89% with ethylene glycol (EG) selectivity of 24.5% and 1.2-PG selectivity of 37.1% and a glycerin selectvity of 8.8%. There is no leaching of any of the components detected from the HOS aqueous product.

The comparisons of the fresh and spent catalyst are listed in Table 12. The catalyst maintained good physical integrity and crush strength.

TABLE 11

The testing conditions and the average catalytic performance for xylitol hydrogenolysis over the NiSb catalyst prepared on nickel-stabilized zirconium oxide (Sample 1).

| Catalyst | NiSb/Sample 1 |
|---|---|
| Operating Conditions | 120 Bar $H_2$ |
| | LHSV: 3 $h^{-1}$ |
| | 210° C. |
| | 25 wt. % Xylitol |
| HOS | 210 h |
| Xylitol Conversion % | 89.2 |
| CS to EG % | 24.5 |
| CS to PG % | 37.1 |
| CS to Gly % | 8.8 |
| Total CS % | 70.5 |

TABLE 12

Characterization of the fresh and spent catalysts for xylitol hydrogenolysis.

| NiSb/No.1 | Composition wt. %[1] | BET S.A. $m^2$/g | P.V. $cm^3$/g | Crush Strength lbs/mm | XRD Phase |
|---|---|---|---|---|---|
| Fresh | Ni: 12.9%; Sb: 0.4 % | 56.3 | 0.31 | 1.8 | NiO; tetragonal $ZrO_2$ |
| spent | Ni: 13.6%. Sb: 0.4% | 93.3 | 0.29 | 1.4 | Ni; tetragonal $ZrO_2$ |

[1]Weight percent of composition calculated on metallic basis.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

We claim:

1. A method for the reduction of a sugar, sugar alcohol or glycerol, the method comprising contacting the sugar, sugar alcohol or glycerol with a hydrogen source and a catalyst comprising:

a ceramic material comprising zirconium oxide and metal oxide, wherein
the zirconium oxide is present in an amount within the range of about 50 wt. % to about 95 wt. % of the ceramic material;
the metal oxide is one or more of nickel oxide, copper oxide, cobalt oxide, iron oxide and zinc oxide, and is present in an amount within the range of about 5 wt. % to about 50 wt. % of the ceramic material, calculated on metallic basis; and a catalytically active metal selected from Ni, Cu, Co, Fe, Ru, Rh, Pd, Ag, Re, Os, Ir, Pt, Au, Sb, La and any combination thereof disposed on the ceramic material, under conditions sufficient to reduce the sugar, sugar alcohol or glycerol.

2. The method of claim 1, wherein the reduction is conducted at a temperature within the range of 180° C. to 600° C., and a pressure within the range of about 1 bar to about 150 bar.

3. The method of claim 1, wherein the reduction is conducted at a temperature in the range of 50° C. to 325° C. and a pressure in the range of about 10 bar to about 250 bar.

4. The method of claim 3, wherein the reduction is conducted at a pH in the range of about 2 to about 6.

5. The method of claim 1, wherein the ceramic material comprises nickel oxide present in an amount within the range of about 5 wt. % to about 40 wt. % of the ceramic material, as calculated on metallic basis.

6. The method of claim 5, wherein the nickel oxide is present in the ceramic material in an amount within the range of about 5 wt. % to about 25 wt. % of the ceramic material, as calculated on metallic basis.

7. The method of claim 5, wherein the nickel oxide is present in the ceramic material in an amount within the range of about 15 wt. % to about 40 wt. % of the ceramic material, as calculated on metallic basis.

8. The method of claim 5, wherein the total amount of zirconium oxide and nickel oxide is at least about 95 wt. % of the ceramic material, as calculated on metallic basis.

9. The method of claim 5, wherein the total amount of zirconium oxide and nickel oxide is at least about 99 wt. % of the ceramic material, as calculated on metallic basis.

10. The method of claim 5, wherein the ceramic material further includes one or more of copper oxide, cobalt oxide, iron oxide and zinc oxide.

11. The method of claim 10, wherein
if present in the ceramic material, the iron oxide is present in an amount within the range of about 5 wt. % to about 30 wt. % of the ceramic material, as calculated on metallic basis,
if present in the ceramic material, the cobalt oxide is present in an amount within the range of about 5 wt. % to about 25 wt. % of the ceramic material, as calculated on metallic basis,
if present in the ceramic material, the copper oxide is present in an amount within the range of about 5 wt. % to about 35 wt. % of the ceramic material, as calculated on metallic basis, and
if present in the ceramic material, the zinc oxide is present in an amount within the range of about 5 wt. % to about 25 wt. % of the ceramic material, as calculated on metallic basis.

12. The method of claim 5, wherein, the iron oxide, the cobalt oxide, the copper oxide and the zinc oxide are not present in the ceramic material.

13. The method of claim 1, wherein the ceramic material comprises
- iron oxide is present in an amount within the range of about 5 wt. % to about 30 wt. % of the material, as calculated on metallic basis;
- cobalt oxide is present in an amount within the range of about 5 wt. % to about 25 wt. % of the material, as calculated on metallic basis;
- copper oxide is present in an amount within the range of about 5 wt. % to about 35 wt. % of the material, as calculated on metallic basis; or
- zinc oxide is present in an amount within the range of about 5 wt. % to about 25 wt. % of the material, as calculated on metallic basis.

14. The method of claim 1, wherein the ceramic material further comprises one one or more additional non-reducible oxides selected from oxides of yttrium, lanthanum, cerium, niobium, tungsten, molybdenum, titanium, calcium, magnesium, boron, tin, anitmony and mixtures thereof, present in a total amount up to about 15 wt. %, calculated on metallic basis for the oxides other than boron and on a boron basis for the oxide of boron.

15. The method of claim 1, wherein the ceramic material further comprises molybdenum oxide, present in a total amount up to about 15 wt. %, calculated on metallic basis.

16. The method of claim 1, wherein the ceramic material further comprises tungsten oxide, present in a total amount up to about 15 wt. %, calculated on metallic basis.

17. The method of claim 1, wherein at least about 80% of the zirconium oxide is in the tetragonal phase, the amorphous phase, or a combination thereof.

18. The method of claim 1, wherein at least about 90% of the zirconium oxide is in the tetragonal phase, the amorphous phase, or a combination thereof.

19. The method of claim 1, wherein the ceramic material is free of cerium oxide.

20. The method of claim 1, wherein the ceramic material is free of manganese.

21. The method of claim 1, wherein the ceramic material is free of chromium.

22. The method of claim 1, wherein the ceramic material is free of silicon oxide, aluminum compounds, silica-alumina compounds, graphite and carbon black.

23. The method of claim 1, wherein the catalyst material has a pore volume within the range of about 0.1 $cm^3/g$ to about 1.0 $cm^3/g$; a surface area within the range of about 10 $m^2/g$ to about 400 $m^2/g$; and a crush strength within the range of about 1.0 lb/mm to about 10 lb/mm.

24. The method of claim 1, wherein the catalyst material is provided as an extrudate.

* * * * *